United States Patent
Singh et al.

(10) Patent No.: US 7,059,181 B2
(45) Date of Patent: Jun. 13, 2006

(54) TEST TO MEASURE CURLING TENDENCY OF PAPER IN LASER PRINTERS

(75) Inventors: Kapil Mohan Singh, Monroe, NY (US); William Shields, Newburgh, NY (US); Frederick Karsa, Basking Ridge, NJ (US)

(73) Assignee: International Paper Co., Stamford, CT (US)

( * ) Notice: Subject to any disclaimer, the term of this patent is extended or adjusted under 35 U.S.C. 154(b) by 53 days.

(21) Appl. No.: 10/705,043

(22) Filed: Nov. 10, 2003

(65) Prior Publication Data

US 2005/0097950 A1 May 12, 2005

(51) Int. Cl.
*G01L 5/04* (2006.01)

(52) U.S. Cl. .................................................. 73/159

(58) Field of Classification Search .................. 73/159, 73/160

See application file for complete search history.

(56) References Cited

U.S. PATENT DOCUMENTS

| | | | |
|---|---|---|---|
| 4,077,519 A * | 3/1978 | Huber | 209/643 |
| 4,747,911 A | 5/1988 | Polson | |
| 5,017,970 A * | 5/1991 | Sakata | 399/67 |
| 5,218,411 A | 6/1993 | Kosugiyama et al. | |
| 5,237,381 A | 8/1993 | Hamada | |
| 5,394,247 A | 2/1995 | Vahey et al. | |
| 5,934,140 A | 8/1999 | Jackson et al. | |
| 5,982,498 A | 11/1999 | Byatt et al. | |
| 6,001,421 A * | 12/1999 | Ahonen et al. | 427/316 |
| 6,094,560 A | 7/2000 | Thomas | |
| 6,244,322 B1 * | 6/2001 | Paque | 156/555 |
| 6,259,888 B1 * | 7/2001 | Kazama et al. | 399/406 |
| 6,322,666 B1 | 11/2001 | Luontama et al. | |
| 2002/0030319 A1 | 3/2002 | Komulainen et al. | |

OTHER PUBLICATIONS

F Nonomura & Y Abe, "A study on the curling behavior of paper resulting from heatroller heating," 1999 TAPPI International Paper Physics Conf., 84-95.

Quality Engineering Associates, Inc., "Toner Fusing Test System," TFS-1000, Burlington, Massachusetts.

* cited by examiner

*Primary Examiner*—Max Noori
(74) *Attorney, Agent, or Firm*—Thomas W. Barnes, III (57) ABSTRACT

The invention provides an apparatus and method for testing the tendency of a paper to curl. The paper is cut from a paper making machine and rapidly humidified to standard TAPPI conditions, and is thereafter run through an apparatus having a substantially vertically oriented nip. The paper is measured for curl, all data are tabulated and fed back into a data acquisition or paper machine control system.

35 Claims, 4 Drawing Sheets

TEST TO MEASURE CURLING TENDENCY OF PAPER IN LASER PRINTERS

FIELD OF THE INVENTION

The present invention relates to a testing instrument and method for measuring the curling tendency of paper in laser printers, photocopiers or other like sheet-fed apparatuses.

BACKGROUND OF THE INVENTION

In a typical laser-based printing/copying process, a photoconductive member is charged to a substantially uniform potential so as to sensitize the surface thereof. The charged portion of the photoconductive member is exposed to a light image of the original document being reproduced. Exposure of the charged photoconductive member selectively dissipates the charges thereon in the irradiated areas. This records a latent image on the photoconductive member corresponding to the informational areas contained within the original document.

One approach to the fixing of toner images onto a support has been to pass the support bearing the toner images between a pair of opposed roller members, at least one of which is internally heated. During operation of a fixing system of this type, the support member to which the toner images are electrostatically adhered is moved through the nip formed between the rolls and thereby heated under pressure. A large quantity of heat is applied to the toner and the copy sheet bearing the toner image. This heat evaporates much of the moisture contained in the sheet. The quantity of heat applied to the front and to the back sides of the sheet is often not equal.

One problem associated with moisture loss in paper is paper curl. Deformation of the paper generally occurs due to a change of physical properties in the z-direction of paper. This may occur through the following event: as sheets pass through an image fixing system, moisture is driven out and the sheet temperature is elevated. After image fixing, a sheet typically rests in a collection area exposed to its ambient surroundings, where its moisture content will reach equilibrium with the environment through absorption of moisture across the full face of at least one side of the paper sheet. However, if the copy sheet becomes part of a large compiled set, both sides of all of the papers in the compilation (except for the top sheet) will effectively be sealed off from ambient moisture. The only route available to the papers for moisture re-absorption is through the edges of the sheets, leaving the moisture content of the central portions of the sheets relatively unchanged. This uneven pattern of moisture re-absorption results in edge stresses that lead to paper curl along the edges of the paper.

Further, contact with moisture can cause curl prior to image fixing. Thus, in addition to being cosmetically unsightly, the curl creates a handling problem, in that pages with a wave pattern along their edges are more difficult to feed to secondary paper handling machines. It is especially important to papers which are used in automatic sheet-fed printing operations such as xerography. Excessive curl can cause the paper transport mechanism to jam, thereby creating operator frustration, lost time and service expense. Therefore, curl is an important mechanical property of non-woven webs such as paper which manufacturers seek to minimize, and there is a continuing need for a measuring device to predict the curl performance of webs which will be used in sheet-fed machines.

Moreover, in sheet-fed apparatuses, curl behavior is further influenced by the heat conductivity of the paper, moisture evaporation from the paper, and the other heating conditions. Thus, curl behavior is influenced by different types of paper as well as different apparatuses used with the same type of paper, resulting in the general unpredictability of the tendency of a paper to curl.

Generally, two types of curl may be generated in paper manufacture as a result of moistening or drying a paper sheet. Total (simplex) curl is when a paper curls in one direction, such as a sheet of paper rolled into a cylindrical tube. Diagonal curl results from a twist of paper, such that one, portion of the paper rotates axially in one direction, while another portion of the paper rotates axially in a different, generally opposite direction.

Current curl tests for prediction of curl tendency are problematic. One procedure involves running multiple sheets through a specified (Xerox 5388) photo copier, hanging a preset number of sheets by the long edge and matching the resulting bend to a pattern of curves on a reference template. This test, however, requires the use of specific, expensive equipment and is costly and time consuming. It also requires that papers be sheeted prior to testing, delaying results.

Hot plate curl is another method currently in use. It involves placing cut samples on a heated hotplate and manually measuring the corners of the sample as they curl away from the heat. This method is time intensive and has very poor ($r^2$ 0.30) correlation to end use as well as poor reproducibility.

Other tests do not account for the ability of gravity to alter the curl of a paper, resulting in errant data. For example, other mechanisms, such as a computer controlled hot-roll fusing apparatus, are able to test for a variety of paper parameters by mimicking the environment of a typical consumer printer, yet the nips are horizontal and have too high nip pressure, resulting in gravitational and mechanical effects on the test samples.

Therefore, it is an object of this invention to provide a test for the tendency of a paper to curl from which information can be achieved quickly and possible corrective feedback is rapid, has a low level of variability, and accounts for the effect of gravity on a tendency to curl for a variety of paper samples.

SUMMARY OF THE INVENTION

Accordingly, the present invention provides a method and apparatus for testing the tendency of a paper to curl in sheet-fed apparatuses comprising moving test paper sheets from a paper making machine, rapidly conditioning the paper sheets to a desired humidity, and moving the paper sheets through a test nip similar to a nip of a sheet-fed apparatus. The nip is positioned substantially vertically so that the paper is substantially vertically positioned when it exits the nip. As, or immediately after, the paper exits the nip, the paper is measured for curl with a measuring means. Corrective curl information is calculated from the curl measurement means, and the information can be relayed back into a paper machine to aid the paper making process to correct for the tendency of a paper to curl.

According to the present invention, the preferred method for measuring the tendency of a paper to curl involves the steps of moving a paper sample from a paper making machine, moving the paper sample through a substantially vertical nip positioned such that the paper sample exits from the substantially vertical nip in a substantially vertical orientation, and measuring the diagonal curl of the paper sample as or after the paper sample exits the substantially vertical nip.

Further embodiments of the invention include adjusting the temperature in the nip such that a sample paper's temperature exiting the nip is between 50–350° F., adjusting the pressure so that the pressure in the nip is minimal, and adjusting the temperature of the nip from a range of 150–450° F. Further, the humidity of the testing environment is controlled such that the sample paper is conditioned in this environment. The measurements are captured by a computer, and final simplex printer curl is predicted by combining the diagonal curl of the paper sample with the moisture content of the paper sample prior to conditioning in the controlled humidity environment in a regression analysis. Corrective information can be obtained from this data and fed back into the paper making machine control panel.

In other embodiments, the invention comprises an apparatus to implement the above method having a nip of two substantially vertically mounted rollers monitored by a computer and located in proximity to a curl measuring means that measures the paper as, or after, it exits the nip in a substantially vertical orientation.

Other objects, embodiments, features and advantages of the present invention will be apparent when the description of a preferred embodiment of the invention is considered in conjunction with the annexed drawings, which should be construed in an illustrative and not limiting sense.

DETAILED DESCRIPTION

Figure 1:
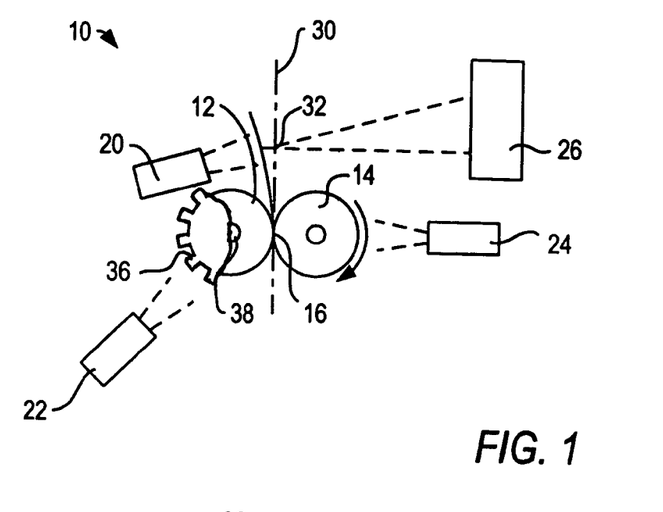
FIG. 1 is a partial top view of an apparatus for testing the tendency of a paper to curl.

An apparatus 10 in accordance with one embodiment of the invention is shown in FIG. 1. Two substantially vertically oriented mounted rollers 12 and 14 are aligned in parallel and close proximity creating a nip point 16 between the rollers. Roller 12 is operably connected to a computer, such that the computer can control the roller's speed, temperature and other variables. In one embodiment, the computer can be programmed to heat roller 12 to a preferred temperature range of 200 to 275° F., although lighter paper grades may require temperature ranges as low as 150° F. and heavier paper grades may require temperature ranges up to 450° F. Generally, the heating of roller 12 is achieved with a heat lamp 38 fixed along the substantially vertical axis of the roller. However, other heat devices may be used within the spirit of the invention. Further, other non-computer controlled heat devices may be used if no computer is available or desired.

Substantially vertically mounted roller 14 is a spring mounted roller mounted in close proximity to substantially vertically mounted roller 12. The spring pressure of roller 14 is zero or minimal and adjusted such that a paper that passes through nip 16 has zero mechanical curl. For the purposes of this application, the term mechanical curl shall mean the amount of curl a paper would have if the rollers defining the nip were unheated. The required spring pressure for roller 14 is adjusted with standard springs and/or spring preloads and can vary from machine to machine, with the desired pressure being the maximum pressure achievable while still maintaining no mechanical curl. As a result, pressure within the nip is zero or minimal even as the rollers are in close proximity. Roller 14 generally does not contain a heat lamp, although one may be included if desired. Further, roller 14 is not necessarily controlled by the computer.

The rollers can be any type of rollers known in the art. Since paper is used in numerous types of apparatuses, other embodiments of the invention test the tendency of the paper to curl where the paper is intended to be used in a variety of apparatuses. This can be achieved by creating a substantially vertical nip that mimics the horizontal nip of the apparatus for which the test paper is intended. The present embodiments, however, are directed to paper intended for a typical xerographic machine, for example, a Xerox 5388 copier, and the related rollers and nips.

The rollers are rotated by a variable speed motor as directed by the computer. The speed can be altered to regulate the total contact time a paper has against the rollers as it passes through the nip, which in turn relates to the heat passed onto the paper in the nip, and the speed of the measuring operation.

The temperature of the rollers and the paper passing between the rollers are monitored by at least one heat sensor. In the embodiment depicted in FIG. 1, three heat sensors are utilized, wherein sensors 20, 22 and 24 monitor the temperature of the paper, roller 12 and roller 14 respectively. Sensor 20 monitors paper temperature as it leaves the nip. The temperature of the paper achieved during the testing process is critical. If the paper falls below the minimum temperature range, the paper will fail to achieve a heated plastic state that permits curl tendency, if any, to dominate. Heat sensors 22 and 24 monitor the individual rollers to maintain the nip at the desired temperature within the preferred temperature range of 200 to 275° F. When the paper passes through the nip point, a transfer of heat occurs between the roller and the paper, thus heating the paper and slightly cooling the rollers. As a result, rapid movement of a multiplicity of paper through the rollers could result in the temperature of the rollers decreasing below the desired range, adversely affecting test results. Temperature sensors prompt a user to temporarily suspend operation when the temperature of the rollers drop, thereby allowing the heating mechanism time to re-stabilize the system. Alternatively, the sensors may be hooked into a feedback loop with the computer such that the computer can automatically correct or compensate for the temperature if it threatens to fall too far from the desired temperature.

In sheet-fed machines, paper is generally heated on one side only, and curl behavior is influenced by the heat conductivity of paper, moisture evaporation from paper and the types of rollers or nips used. Thus, the types of nips, rollers, temperature range and speed can be adjusted depending on the type of paper being tested and the type of instrument with which the paper is intended to be used.

A theoretical centerline 30 extends outwardly from the nip, perpendicular to rollers 12 and 14. Two standard laser sensors 26 and 28 are positioned in parallel in a substantially vertical plane at a distance from the nip such that parallel lasers are emitted from the two sensors crossing centerline 30 along points 32. Points 32 are preferably in close proximity to the nip point such that the paper can be measured for curl immediately after it leaves the nip. In the present embodiment, the distance between the nip and points 32 is about 37 mm. The exact distance can vary by several mm. However, if points 32 is too close to the nip point, no curl will be recorded by the lasers.

The distance between the lasers and the nip can vary as long as it is within the range of the sensors. The laser sensors emit laser beams toward the paper as or immediately after it leaves the nip, and curl is measured regardless of which direction the paper curls. For example, if the paper curls toward heated roller 12, the laser sensors report a positive value. Conversely, if the paper curls toward the pressure roller 14, a negative value is obtained. Alternatively, if the paper does not curl, calculations will reveal a zero value.

Feed slot 58 is located in operable connection with rollers 14 and 16. Testing paper is loaded into the feed slot, and in turn is fed into the nip point. The feed slot can take the form of any device known in the art that can hold and feed paper into a nip point. The feeder design must not inhibit or promote curl.

Figure 2:
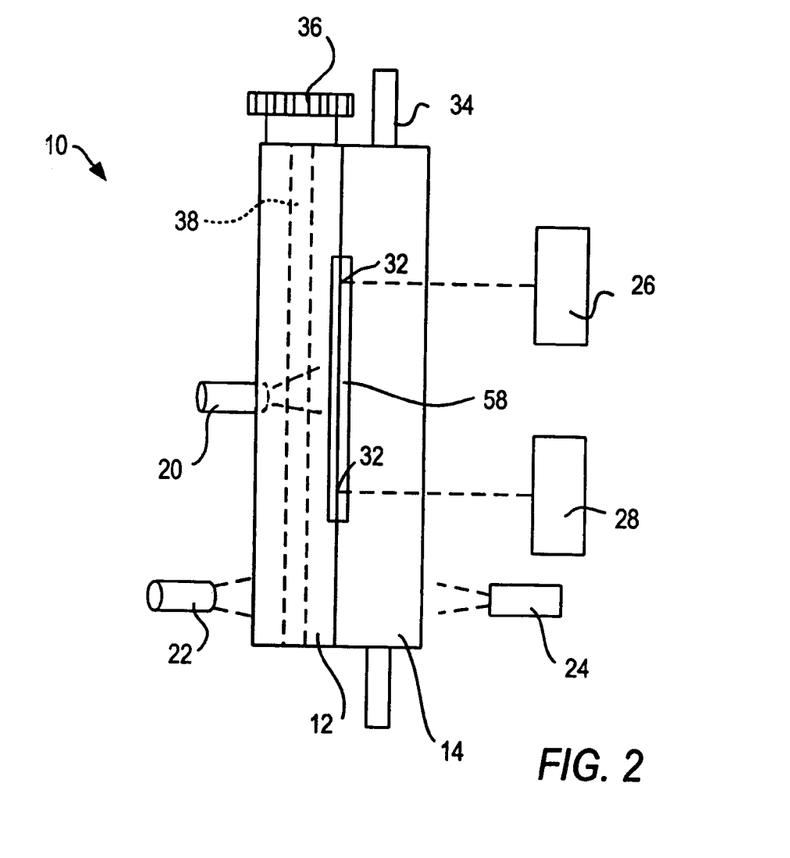
FIG. 2 is a partial side view of an apparatus for testing the tendency of a paper to curl.

FIG. 2 depicts an alternate view of the embodiment. Laser sensors 26 and 28 emit lasers toward the centerline that are parallel to each other, in different horizontal planes, and perpendicular to centerline 30. They are preferably about 3–5 inches apart in the substantially vertical plane. However, the exact distance can vary within the spirit of the invention. Further, in FIG. 2, the mounting devices of the rollers are pictured. Pressure roller 16 is mounted on pressure bearing springs 34. Drive gear 36 is operably connected to roller 12 and is further connected to a motor 52 or other mechanical device that engages the drive gear. When the motor is activated, the drive gear is rotated, which in turn rotates roller 12.

The preferred embodiment of the method for measuring the tendency of a paper to curl involves moving a paper sample from a standard paper making machine to the apparatus above, and then moving the paper sample through the substantially vertical nip positioned such that the paper sample exits from the substantially vertical nip in a substantially vertical orientation, and then measuring the diagonal curl of the paper sample as or after the paper sample exits the substantially vertical nip. The paper samples may be moved from the paper, making machine in an automated in-line process or they may be physically carried from the paper making machine to the substantially vertical nip of FIGS. 1–2.

Further embodiments of the method involve humidifying the paper samples to a known humidity prior to moving the paper through the substantially vertical nip. This can be achieved by moving the paper to a room with controlled ambient air humidity and temperature. Further, the substantially vertical nip may be at a controlled humidity and temperature, such that the paper is conditioned and maintained at the known moisture content.

Figure 3A:
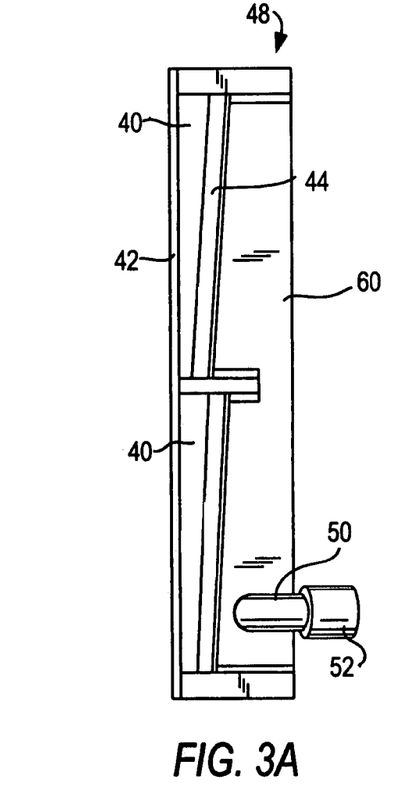
FIG. 3a is a partial side view of one embodiment of a rapid conditioner system.
Figure 3B:
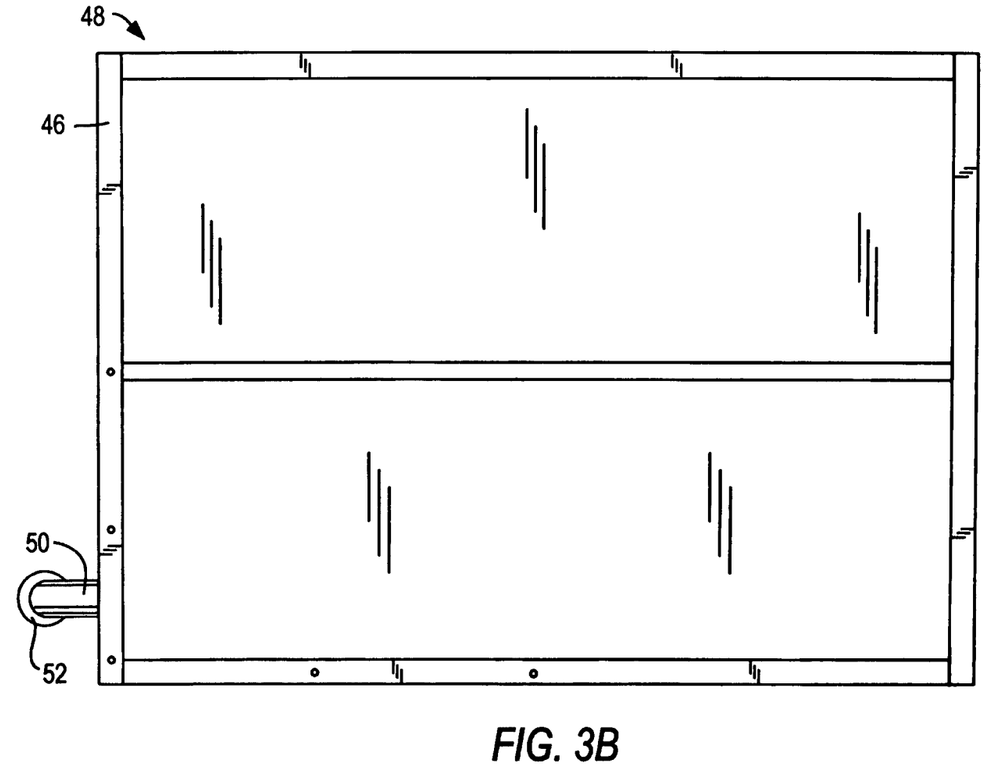
FIG. 3b is a partial front view of one embodiment of a rapid conditioner system.

Alternatively, or additionally, one embodiment of the machinery utilized for testing the tendency of a paper to curl is depicted in FIGS. 3a–b. FIGS. 3a and 3b depicts a rapid conditioning system 48 having void 60 defined by an solid outer wall, solid side walls 46, and angled inner wall 44. A vacuum pump 50 is connected to the interior of the void 60 with tubing through a fitting in one of the sides. The present embodiment contains a multiplicity of angled inner walls 44 to increase the speed of the conditioning process. However, a conditioning system having a single inner wall is within the teachings of the invention.

Outer and side walls 42 and 46 are made of any non-permeable substance, for example, plywood, and are further preferably sealed with silicone. Additionally, the thickness of the outer and side walls can vary greatly. For cost efficiency, however, the present embodiment includes a thickness of about ¼ of an inch. The angled walls are preferably made of permeable substance. In the present embodiment, the angled walls have a back side of perforated plastic sheets that are about ⅛ of an inch thick with a 50% hole pattern (wherein the material is 50% hole area and 50% plastic), covered by a front side having about ½ inch of open inch cell foam. The materials and/or thickness of the materials are variable as long as the material retains a form of permeability.

The method for predicting the tendency of a paper to curl can have paper samples move from the paper making machine to the humidifier to the substantially vertical nip in a single automated in-line process. Other method embodiments include physically moving the paper samples from one apparatus to another, or a combination of in-line and physical movement. One preferred embodiment includes the following. Paper samples from a paper making machine are removed from the machine and cut into 8½×8½ inch sheets. The sheets are brought to the rapid conditioner system of FIGS. 3a–3b. Up to six sheets are placed on the front of the angled sides 44. The vacuum pump is activated, drawing the ambient humidified air through the tester sheets and the angles walls, thereby rapidly conditioning the test sheets to the ambient air humidity, preferably standard TAPPI conditions of 70° F. and 50% relative is humidity. The humidity conditioning process lasts for about five minutes, after which the vacuum pump is deactivated and the conditioned test samples are removed. The vacuum may be operably connected to a timer system that automatically deactivates the vacuum after five minutes or another set time interval. Alternatively, the vacuum may be deactivated manually. In further embodiments, the rapid conditioner system includes a humidity sensor that shuts off the system when a desired humidity is reached in the paper.

Figure 4:
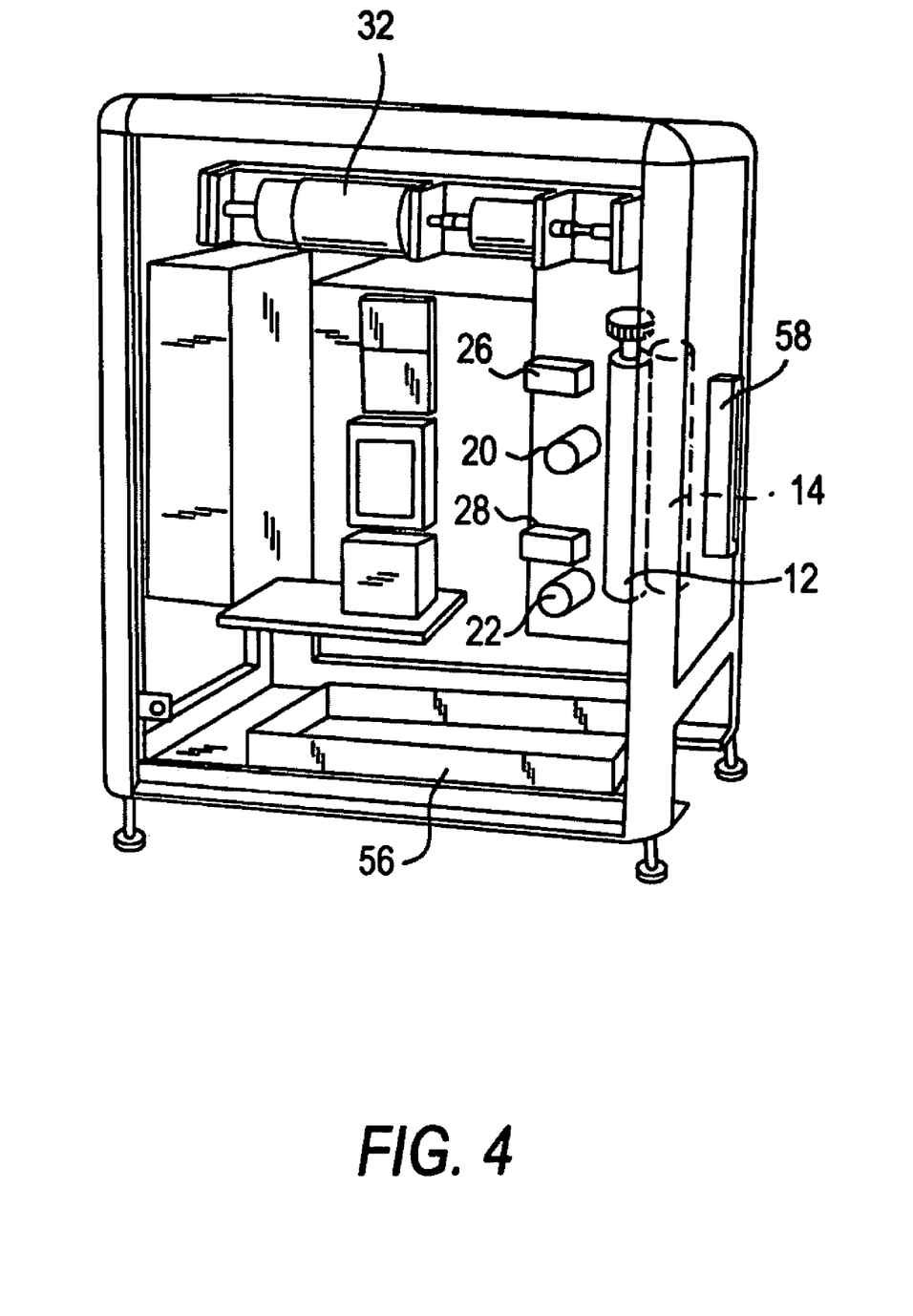
FIG. 4 is a full perspective view of one embodiment of an apparatus for testing the tendency of a paper to curl.

After conditioning, the conditioned test papers are removed from the humidity conditioning system and further cut into sheets about 4½×4½ inches, although the exact size may vary. The temperature in the nip is adjusted by programming the computer to activate the heating lamp, thereby heating the roller 14 within the range of 150–450° F. The spring pressure of roller 16 is adjusted to the maximum allowable pressure wherein pressure within the nip is minimal such that there would be no mechanical curl on a paper put through the nip if the rollers were not heated. The newly cut and humidified sheets are manually carried to the curl tester 10, one embodiment of which is depicted in FIG. 4.

The paper samples are placed into the feed tray 58 of the curl testing unit, which holds the test paper in an substantially vertical, oblong orientation. The feed tray feeds the substantially vertically oriented test paper between the substantially vertically oriented rollers, which heat the test paper to 165° F. or another specific desired temperature, preferably within the range of 50–350° depending on the paper grade. As the paper exits, the nip laser sensors 26 and 28 emit parallel laser beams that measure deviation of the paper from the centerline. The two sensor readings are used to calculate the total curl of the paper, the sum of both laser sensor readings, and the diagonal curl of the paper, the absolute difference between the two laser sensor readings. Upon fully exiting the nip, the test papers drop into catch tray 56 for easy removal.

The simplex curl tendency of a paper is calculated by combining the moisture content of the test paper with the total curl values of the test paper. In one embodiment, a regression analysis equation used to calculate tendency to curl is $$Sx\ Max = 325 - 142*(Moisture) + 15.6*(MoistSQ) + 0.341\ Total\ Crl$$

wherein Sx Max=the Maximum simplex curl in a targeted xerographic machine, Moisture=the ambient moisture found in a newly opened ream of paper, MoistSQ=the square of the ream moisture, and Crl=the diagonal curl measured form the curl tester. The equation has an r-square of 76.5%.

Other empirically developed equation s can be arrived at depending on what type of apparatus with which the test papers are meant to be used. In one test, thirty six sample papers were put through the curl tester and diagonal curl was measured, as shown in TABLE 1.

ratuses. Further, corrective data can be tabulated from the predicted tendency to correct the tendency of a non-sample paper to curl in a paper making machine. The corrective information is then fed back into a data acquisition or paper making machine control system. The calculated data can be used to correct curl tendency by controlling head box rush/drag ratios and jet profiles in a paper making machine as known in the art. In other embodiments, the data can be automatically fed into a paper making machine with a feed back loop to the paper making machine.

Although the invention has been described with reference to preferred embodiments, it will be appreciated by one of ordinary skill in the art that numerous modifications are possible in light of the above disclosure. For example, the nip can be any kind of nip known in the art, as long as it is substantially vertically oriented. All such variations and modifications are intended to be within the scope and spirit of the invention as defined in the claims appended hereto.

TABLE 1

| Sample Number | Sample | Actual Maximum Simplex curl on Xerox 5388, Felt Side or Wire Side | Predicted SxMax with Moisture, Moisture Square and Fuser Curl | Fuser Curl Tester Reading | Ream Moisture, measured ahead of Xerox 5388 Curl Test | (Ream Moisture) Squared |
|---|---|---|---|---|---|---|
| 1 | 20# Benchmarking A1 | 12.5 | 14.8 | 20 | 5.18 | 26.8324 |
| 2 | 20# Benchmarking A2 | 17.5 | 14.4 | 24 | 5.08 | 25.8064 |
| 3 | 20# Benchmarking A3 | 12.5 | 12.5 | 28 | 4.81 | 23.1361 |
| 4 | 20# Benchmarking B2 | 20.0 | 20.4 | 43 | 5.05 | 25.5025 |
| 5 | 20# Benchmarking B3 | 15.0 | 16.6 | 30 | 5.09 | 25.9081 |
| 6 | 20# Benchmarking C1 | 22.5 | 15.3 | 28 | 5.05 | 25.5025 |
| 7 | 20# Benchmarking C3 | 17.5 | 14.5 | 27 | 5.02 | 25.2004 |
| 8 | 20# Benchmarking C5 | 22.5 | 18.8 | 36 | 5.1 | 26.01 |
| 9 | 20# Benchmarking D1 | 27.5 | 23.4 | 27 | 5.44 | 29.5936 |
| 10 | 20# Benchmarking D2 | 27.5 | 20.3 | 36 | 5.18 | 26.8324 |
| 11 | 20# Benchmarking E1 | 15.0 | 21.3 | 40 | 5.16 | 26.6256 |
| 12 | 20# Benchmarking E2 | 30.0 | 18.2 | 37 | 5.04 | 25.4016 |
| 13 | 20# Benchmarking W1 | 20.0 | 17.1 | 41 | 4.84 | 23.4256 |
| 14 | 20# Benchmarking W2 | 25.0 | 16.5 | 41 | 4.75 | 22.5625 |
| 15 | 20# Benchmarking W3 | 22.5 | 18.2 | 45 | 4.3 | 18.49 |
| 16 | 24# Benchmark A-1 | 20.0 | 9.7 | 16 | 4.16 | 17.3056 |
| 17 | 24# Benchmark B-1 | 12.5 | 13.5 | 29 | 4.22 | 17.8084 |
| 18 | 24# Benchmark C1–30 | 15.0 | 15.6 | 31 | 4.1 | 16.81 |
| 19 | 24# Benchmark C1–35 | 15.0 | 13.2 | 33 | 4.62 | 21.3444 |
| 20 | 24# Benchmark D-1 | 10.0 | 9.8 | 13 | 4.08 | 16.6464 |
| 21 | 24# Benchmark E-1 | 12.5 | 10.8 | 22 | 4.25 | 18.0625 |
| 22 | 24# Benchmark GP-1 | 15.0 | 12.2 | 27 | 4.28 | 18.3184 |
| 23 | C30 Size Press Trial - 30H15051E | 20.0 | 18.9 | 40 | 5.02 | 25.2004 |
| 24 | C30 Size Press Trial - 30H15071E | 17.5 | 16.1 | 32 | 5.01 | 25.1001 |
| 25 | C30 Size Press Trial - 30H15093E | 15.0 | 13.7 | 33 | 4.74 | 22.4676 |
| 26 | C35 Normal Paper | 27.5 | 20.2 | 32 | 5.24 | 27.4576 |
| 27 | Eastover Profile 4L | 20.0 | 17.0 | 34 | 5.03 | 25.3009 |
| 28 | Eastover Profile A1 | 22.5 | 21.1 | 54 | 4.78 | 22.8484 |
| 29 | Eastover Profile A2 | 22.5 | 17.6 | 45 | 4.71 | 22.1841 |
| 30 | Eastover Profile X7 | 15.0 | 2.0 | | 4.64 | 21.5296 |
| 31 | Eastover Profile X8 | 20.0 | 19.0 | 50 | 4.62 | 21.3444 |
| 32 | Eastover Relicopy | 10.0 | 10.5 | 25 | 4.63 | 21.4369 |
| 33 | Ray Clements Box #1 | 37.5 | 34.7 | 42 | 5.64 | 31.8096 |
| 34 | Ray Clements Box 17 | 40.0 | 30.7 | 46 | 5.47 | 29.9209 |
| 35 | Ray Clements Box 690 | 30.0 | 30.1 | 46 | 5.45 | 29.7025 |
| 36 | Relizon/Eastover Curl Complaint | 40.0 | 38.8 | 53 | 5.65 | 31.9225 |

Figure 5:
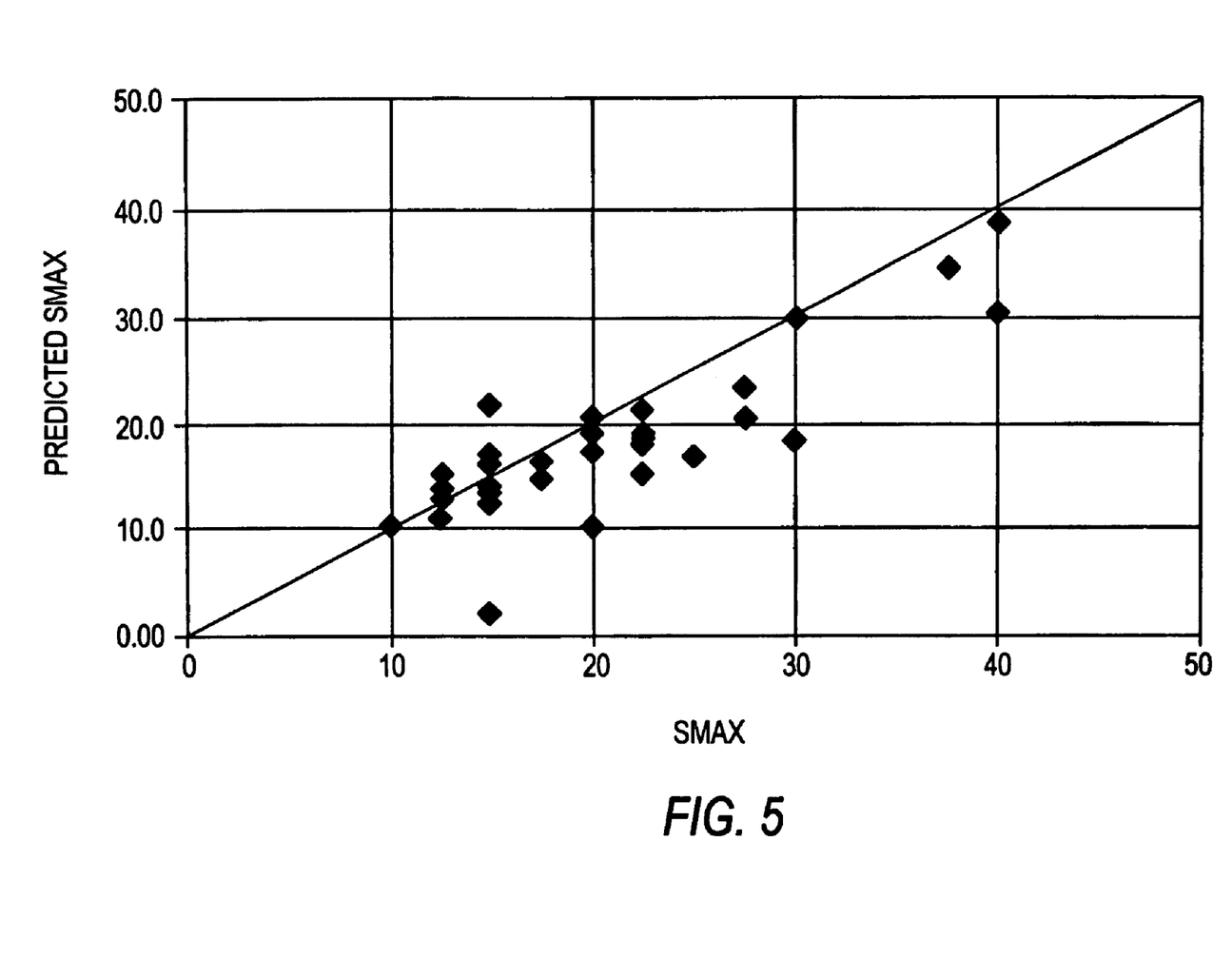
FIG. 5 is a chart showing a analysis of predicted simplex curl vs. actual simplex curl.

Plotted out in the graph shown in FIG. 5, the predicted simplex curl of each sample point except point 30 (missing value) is compared to actual measure simplex curl. The resultant standard deviation of the predicted curl from the actual curl is lower than 5%.

The tendency of a paper to simplex curl can be predicted for standard laser printers, photocopiers or other like appa-

We claim:

1. A method for measuring the tendency of a paper to achieve simplex curl, comprising the steps of: moving a paper sample from a paper making machine through a substantially vertical nip positioned such that the paper sample exits from the substantially vertical nip in a substantially vertical orientation, measuring the diagonal curl of the paper sample as or after the paper sample exits the substantially vertical nip, and predicting the tendency of a paper to simplex curl with a regression analysis equation that accounts for the moisture content of the paper sample and the diagonal curl of the paper sample.

2. The method of claim 1, further comprising the step of maintaining the substantially vertical nip and the paper sample at a controlled humidity and temperature, such that the paper is conditioned by the humidity and temperature to achieve a known moisture content.

3. The method of claim 1, further comprising the step of conditioning the paper sample to a known moisture content prior to moving the paper sample through the substantially vertical nip.

4. The method according to claim 1, further comprising heating the paper sample.

5. The method according to claim 1, further comprising heating the paper sample as or after it leaves the substantially vertical nip.

6. The method of claim 1, further comprising the step of tabulating corrective data to correct the tendency of a non-sample paper to curl in the paper making machine based on the predicted final printer curl.

7. The method of claim 6, further comprising the step of feeding the corrective data into a data acquisition or paper making machine control system.

8. The method of claim 1, wherein the step of measuring the curl of the paper sample as or after the paper sample exits the substantially vertical nip is achieved by measuring the diagonal curl of a paper with a diagonal curl measuring device immediately as or after the paper leaves the substantially vertical nip.

9. The method of claim 8, wherein the diagonal curl measuring device is a multiplicity of lasers directed at the paper sample.

10. The method of claim 1, wherein the substantially vertical nip is heated.

11. The method of claim 10, wherein the substantially vertical nip is heated to a minimum temperature of 150° F.

12. The method of claim 10, wherein the substantially vertical nip is heated to a maximum temperature of 450° F.

13. The method of claim 10, wherein the substantially vertical nip is heated to a temperature between 200–400° F.

14. The method of claim 1, wherein the paper sample as or after it leaves the substantially vertical nip is heated to a minimum temperature of 50° F.

15. The method of claim 1, wherein the paper sample as or alter it leaves the substantially vertical nip is heated to a maximum temperature of 350° F.

16. The method of claim 1, wherein the paper sample as or after it leaves the substantially vertical nip is heated to a temperature between 50–350° F.

17. The method of claim 1, wherein the pressure in the substantially vertical nip is minimal such that there is no diagonal curl in the sample paper if the substantially vertical nip was not heated.

18. The method of claim 1, wherein a multiplicity of paper samples are sequentially moved though the substantially vertical nip.

19. An apparatus for measuring the tendency of a paper or paperboard to curl in a printer having a substantially vertical nip and used interconnected with a paper making machine, comprising: a rotatable first roller, wherein the first roller is rotatable around a first substantially vertical axis in a substantially vertical plane, a rotatable second roller, wherein the second roller is rotatable around a second substantially vertical axis in the substantially vertical plane, the first substantially vertical axis parallel to the second substantially vertical axis, and the first and second rollers rotatable in opposing directions a substantially vertical nip point between the first roller and the second roller such that a paper or paperboard can pass through the substantially vertical nip point, a measuring means for measuring a diagonal curl of the paper or paperboard, and a means for predicting tendency of a paper to simplex curl with a regression analysis equation that accounts for the moisture content of the paper sample and the diagonal curl of the paper sample.

20. The apparatus according to claim 19, further comprising a means for heating the paper or paperboard to a temperature between 50 and 350° F. as or after the paper or paperboard leaves the substantially vertical nip.

21. The apparatus according to claim 19, further comprising a means for maintaining the substantially vertical nip and the paper or paperboard at a controlled humidity and temperature, such that the paper is conditioned by the humidity and temperature to achieve a known moisture content.

22. The method of claim 19, further comprising a means for conditioning the paper or paperboard to a known moisture content prior to moving the paper or paperboard through the substantially vertical nip.

23. The apparatus according to claim 19, further comprising a means for tabulating corrective data to correct the tendency of a following paper or paperboard to curl in the paper making machine based on the predicted final printer curl.

24. The apparatus according to claim 23, further comprising a means for feeding the corrective data into a data acquisition or paper making machine control system.

25. The apparatus according to claim 19, wherein the means for measuring the curl of the paper or paperboard is achieved by measuring the diagonal curl of a paper with a diagonal curl measuring device immediately as or after the paper leaves the substantially vertical nip.

26. The apparatus according to claim 25, wherein the diagonal curl measuring device comprises at least one of laser directed at the paper or paperboard.

27. The apparatus according to claim 19, wherein the substantially vertical nip is a heated substantially vertical nip.

28. The apparatus according to claim 19, wherein the substantially vertical nip is at a minimum temperature of 150° F.

29. The apparatus according to claim 19, wherein the substantially vertical nip is at a maximum temperature of 450° F.

30. The apparatus according to claim 19, wherein the substantially Vertical nip is at a temperature between 200° F. and 400° F.

31. The apparatus according to claim 19, further comprising a means for heating the paper or paperboard as or after the paper or paperboard leaves the substantially vertical nip.

32. The apparatus according to claim 19, further comprising a means for heating the paper or paperboard.

33. The apparatus according to claim 19, further comprising a means for heating the paper or paperboard to a minimum temperature of 50° F.

34. The apparatus according to claim 19, further comprising a means for heating the paper or paperboard to a minimum temperature of 50° F. as or after the paper or paperboard leaves the substantially vertical nip.

35. The apparatus according to claim 19, further comprising a means for heating the paper or paperboard to a maximum temperature of 350° F. as or after the paper or paperboard leaves the substantially vertical nip.

* * * * *